US012611150B2

(12) United States Patent
Yoshida et al.

(10) Patent No.: US 12,611,150 B2
(45) Date of Patent: Apr. 28, 2026

(54) X-RAY INSPECTION APPARATUS AND INSPECTION METHOD OF X-RAY SENSOR UNIT

(71) Applicant: ISHIDA CO., LTD., Kyoto (JP)

(72) Inventors: Keisuke Yoshida, Ritto (JP); Futoshi Yurugi, Ritto (JP); Osamu Hirose, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 141 days.

(21) Appl. No.: 18/605,799

(22) Filed: Mar. 14, 2024

(65) Prior Publication Data

US 2024/0407742 A1    Dec. 12, 2024

(30) Foreign Application Priority Data

Mar. 20, 2023    (JP) ................................ 2023-044623

(51) Int. Cl.
*A61B 6/00*      (2024.01)
*A61B 6/40*      (2024.01)
*A61B 6/42*      (2024.01)
(52) U.S. Cl.
CPC .......... *A61B 6/4035* (2013.01); *A61B 6/4241* (2013.01); *A61B 6/54* (2013.01)
(58) Field of Classification Search
CPC ............................................. G01N 2223/643
See application file for complete search history.

(56) References Cited

U.S. PATENT DOCUMENTS

| | | | | |
|---|---|---|---|---|
| 2019/0212273 A1* | 7/2019 | Scoullar | .................... | G01J 3/28 |
| 2020/0363347 A1* | 11/2020 | Siegrist | ................. | G01N 33/02 |
| 2021/0148837 A1* | 5/2021 | Takeda | .................... | G01N 23/04 |
| 2023/0284991 A1 | 9/2023 | Iwakawa et al. | | |

FOREIGN PATENT DOCUMENTS

| | | |
|---|---|---|
| JP | H1-116410 A | 1/1999 |
| JP | 2023-132587 A | 9/2023 |

OTHER PUBLICATIONS

Extended Search Report in the corresponding European Patent Application No. 24163954.1 dated Jul. 12, 2024.

* cited by examiner

*Primary Examiner* — Dani Fox
(74) *Attorney, Agent, or Firm* — Spencer Fane LLP

(57)         ABSTRACT
An X-ray inspection apparatus includes an irradiation unit configured to irradiate a conveyed article with X-rays, an X-ray sensor unit including a sensor unit configured to detect the X-rays by photon counting and an image generation unit configured to generate an image based on a detection result output from the sensor unit, and a control unit having a first mode for inspecting the article based on the image and a second mode for determining a state of the X-ray sensor unit at a time of time delay integration driving, in which the control unit is configured to compare a first image generated based on a detection result output from the sensor unit at a time t1 with a second image generated by integrating detection results output from the sensor unit until a time t2 after the time t1 to determine the state of the X-ray sensor unit.

4 Claims, 6 Drawing Sheets

X-RAY INSPECTION APPARATUS AND INSPECTION METHOD OF X-RAY SENSOR UNIT

CROSS REFERENCE TO RELATED APPLICATIONS

This application claims the benefit of priority to Japanese Patent Application Number 2023-044623 filed on Mar. 20, 2023. The entire contents of the above-identified application are hereby incorporated by reference.

TECHNICAL FIELD

One aspect of the present disclosure relates to an X-ray inspection apparatus and an inspection method of an X-ray sensor unit.

BACKGROUND

Japanese Unexamined Patent Publication No. H1-116410 discloses an optical sensor having a self-diagnosis function including a light emission amount setting unit configured to set a light emission amount of a light emitting element, a current control unit configured to perform current control of a current flowing through the light emitting element based on the set light emission amount, and an abnormality detection unit configured to compare the set light emission amount with a detection signal corresponding to the light emission amount and detect an abnormality of the optical sensor.

SUMMARY

In an X-ray inspection apparatus, a sensor unit capable of detecting X-rays by photon counting may be used. In such a sensor unit, there may be a defective product whose output decreases when being driven by a time delay integration method (TDI method). Here, the sensor unit outputs normally at the time of normal driving in many cases. Therefore, it may be overlooked that the X-ray inspection apparatus includes a sensor unit that may cause a defect at the time of TDI driving. Therefore, there is a demand for a method capable of determining whether or not the X-ray inspection apparatus includes an X-ray sensor unit that outputs normally at the time of normal driving but shows decrease in output at the time of time delay integration driving.

An object of one aspect of the present disclosure is to provide an X-ray inspection apparatus and an inspection method of an X-ray sensor unit capable of satisfactorily determining a state of the X-ray sensor unit at the time of time delay integration driving.

(1) An X-ray inspection apparatus according to one aspect of the present disclosure includes a conveyance unit configured to convey an article, an irradiation unit configured to irradiate the article conveyed by the conveyance unit with X-rays, an X-ray sensor unit including a sensor unit configured to detect the X-rays by photon counting and an image generation unit configured to generate an image based on a detection result output from the sensor unit, and a control unit having a first mode for inspecting the article based on the image and a second mode for determining a state of the X-ray sensor unit at a time of time delay integration driving, in which in the second mode, the sensor unit is configured to detect X-rays not transmitted the article, and the control unit is configured to compare a first image generated based on a detection result output from the sensor unit at a time t1 with a second image generated by integrating detection results output from the sensor unit until a time t2 after the time t1 to determine the state of the X-ray sensor unit at the time of time delay integration driving.

According to the X-ray inspection apparatus, in the second mode, the first image generated based on the detection result output from the sensor unit at the time t1 is compared with the second image generated by integrating the detection results output from the sensor unit until the time t2 after the time t1. As a result, it is possible to compare an output of the sensor unit at the time of normal driving with an output of the sensor unit at the time of time delay integration driving. By using this comparison, for example, it is possible to easily determine whether or not there is a defect in the X-ray sensor unit at the time of time delay integration driving. Therefore, by using the X-ray inspection apparatus, the state of the X-ray sensor unit at the time of time delay integration driving can be satisfactorily determined.

(2) The X-ray inspection apparatus described in (1) above may further include a sensitivity correction unit configured to perform sensitivity correction of the sensor unit based on the X-rays not transmitted the article, and when the sensitivity correction is performed by the sensitivity correction unit, the control unit may be configured to determine the state of the X-ray sensor unit at the time of time delay integration driving. In this case, for example, before the inspection of the article by the X-ray inspection apparatus, the state of the X-ray sensor unit at the time of time delay integration driving can be satisfactorily determined.

(3) In the X-ray inspection apparatus described in (1) or (2) above, the control unit may be configured to determine that the X-ray sensor unit is defective when the second image is darker than the first image by a predetermined ratio or more.

(4) In the X-ray inspection apparatus described in any one of (1) to (3) above, in the second mode, the control unit may be configured to determine a transmission state from the sensor unit to the image generation unit at the time of time delay integration driving or a state of an image generation operation by the image generation unit at the time of time delay integration driving.

(5) An inspection method of an X-ray sensor unit according to another aspect of the present disclosure is an inspection method of an X-ray sensor unit including a sensor unit configured to detect X-rays by photon counting and an image generation unit configured to generate an image based on a detection result output from the sensor unit, the inspection method including, comparing a first image generated based on a detection result output from the sensor unit at a time t1 with a second image generated by integrating detection results output from the sensor unit until a time t2 after the time t1, and determining a state of the X-ray sensor unit at the time of time delay integration driving.

According to this inspection method, the first image generated based on the detection result output from the sensor unit at the time t1 is compared with the second image generated by integrating the detection results output from the sensor unit until the time t2 after the time t1. As a result, it is possible to compare an output of the sensor unit at the time of normal driving with an output of the sensor unit at the time of time delay integration driving. By using this comparison, for example, it is possible to easily determine whether or not there is a defect in the X-ray sensor unit at the time of time delay integration driving. Therefore, the state of the X-ray sensor unit at the time of time delay integration driving can be satisfactorily determined by using the inspection method.

According to one aspect of the present disclosure, it is possible to provide an X-ray inspection apparatus and an inspection method of an X-ray sensor unit capable of satisfactorily determining a state of the X-ray sensor unit at the time of time delay integration driving.

DETAILED DESCRIPTION

Figure 1:
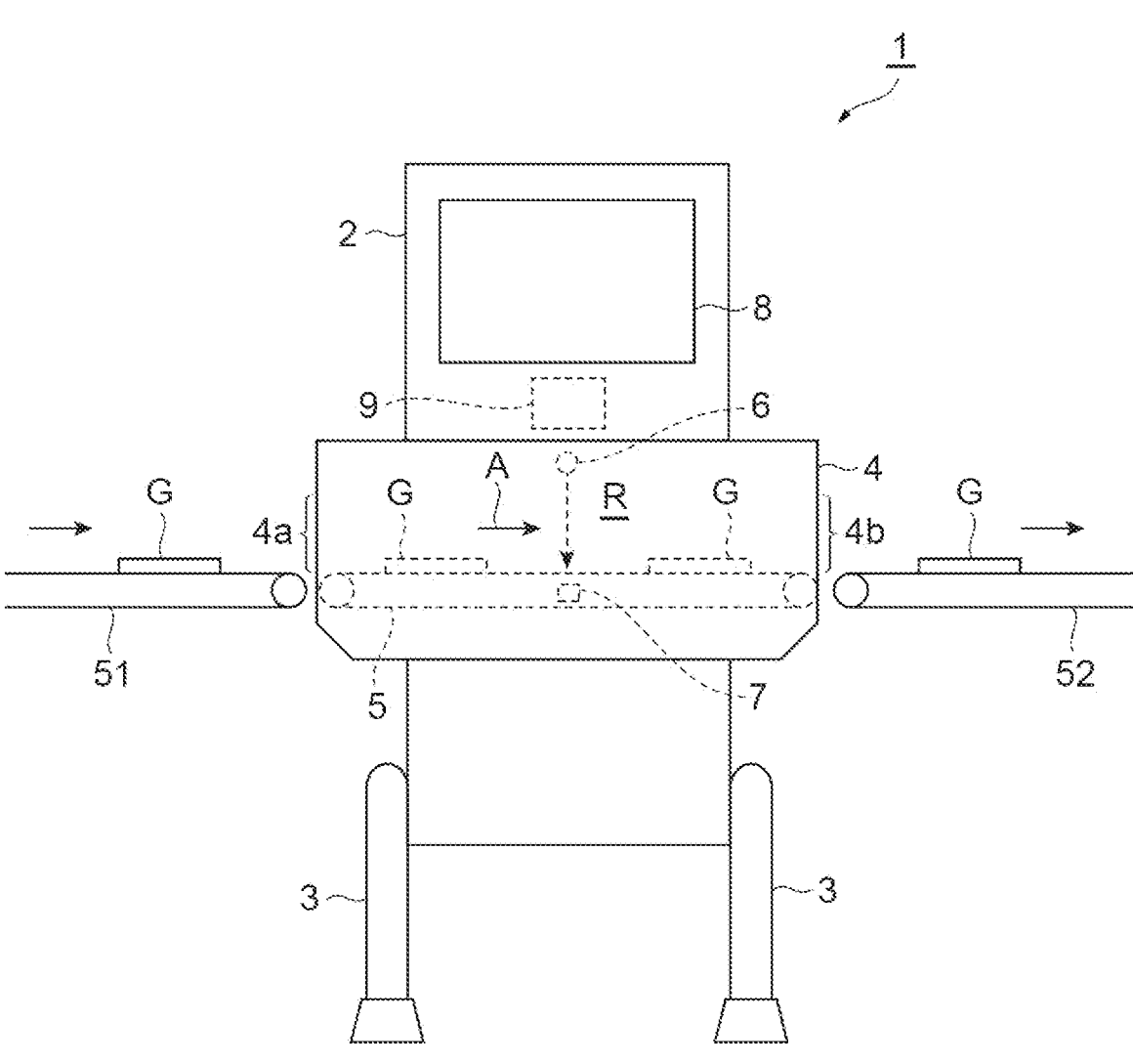
FIG. 1 is a configuration diagram of an X-ray inspection apparatus according to an embodiment.

Hereinafter, a preferred embodiment of the present disclosure will be described in detail with reference to the accompanying drawings. In the description of the drawings, the same or corresponding elements are denoted by the same reference numerals, and redundant description is omitted. In the claims and the specification, the phrase "A or B" means that either A or B is included, and it is also acceptable to include both A and B.

Figure 2:
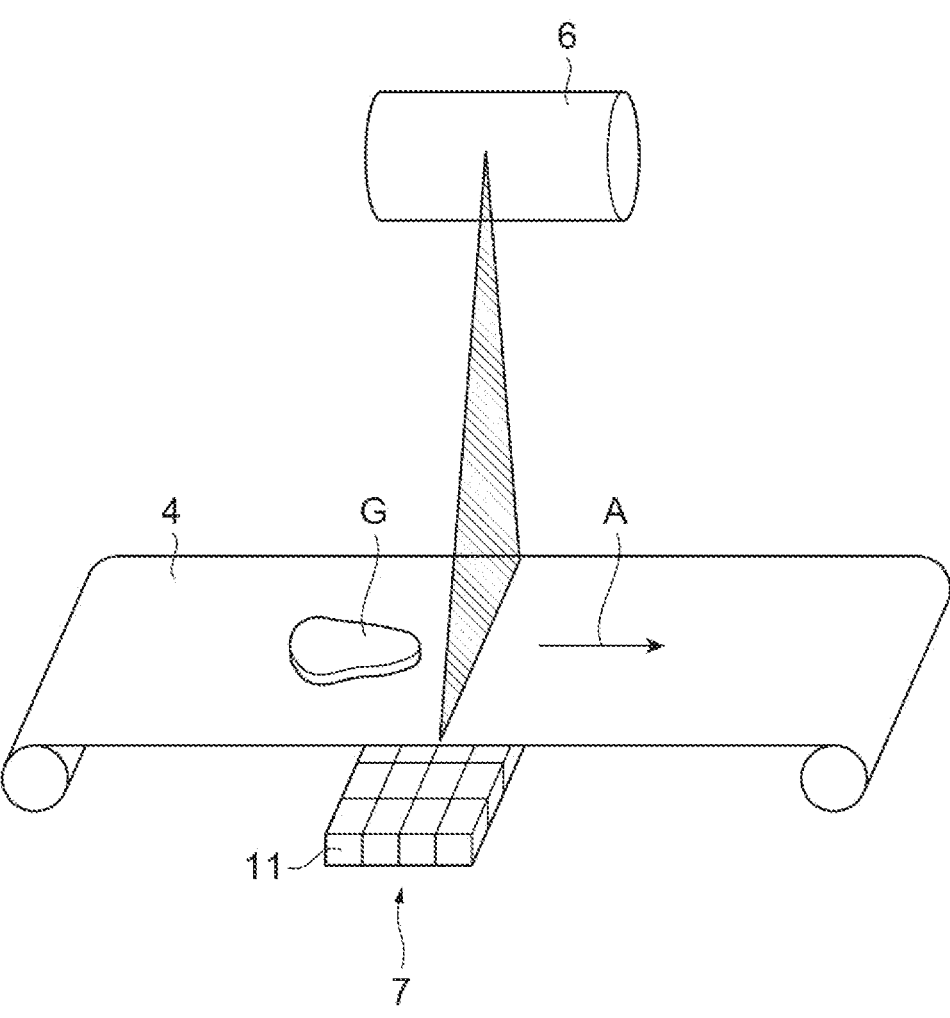
FIG. 2 is a schematic configuration diagram of an inside of a shield box illustrated in FIG. 1.
Figure 3:
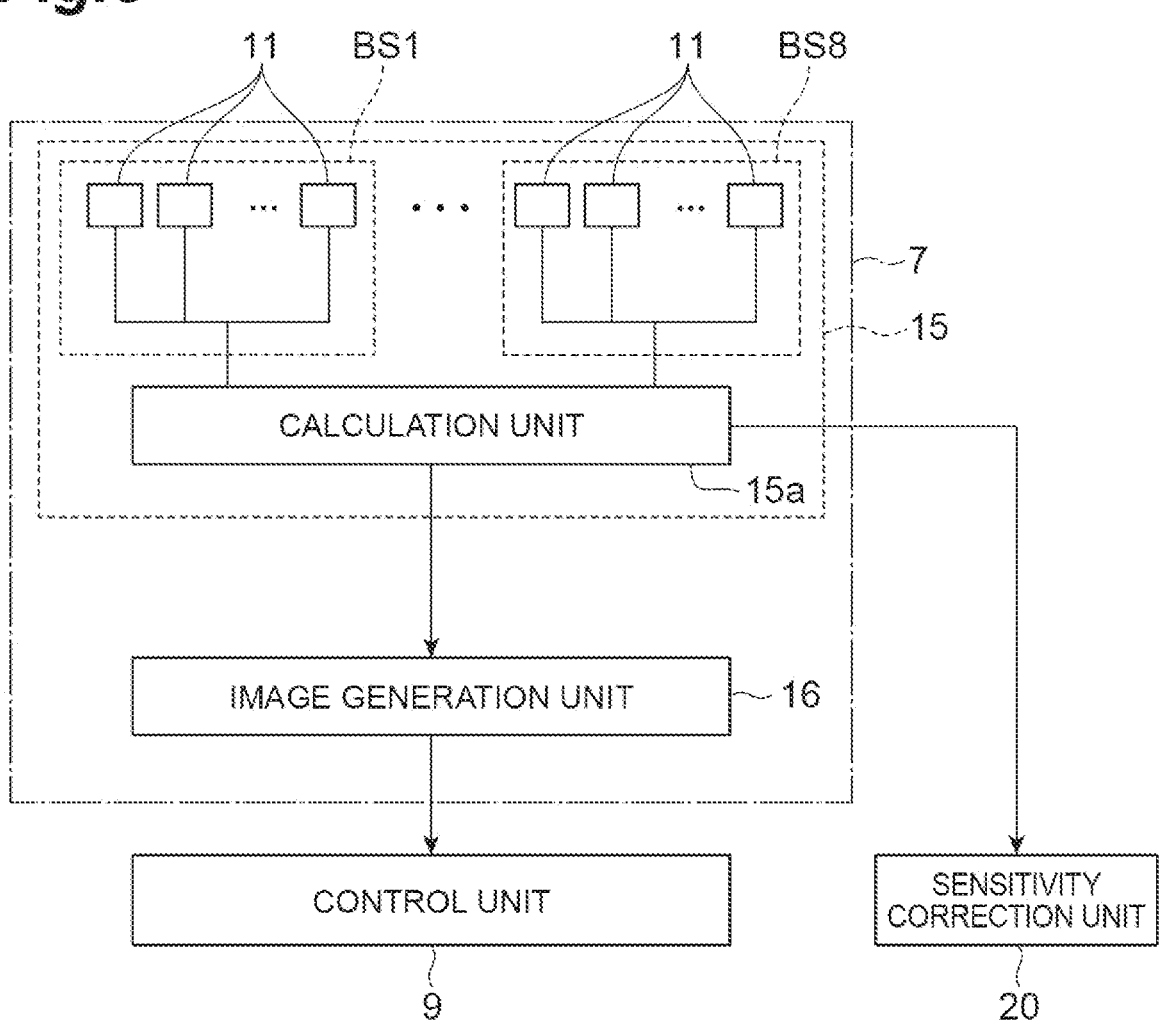
FIG. 3 is a block diagram illustrating an X-ray sensor unit, a control unit, and a sensitivity correction unit provided in the X-ray inspection apparatus.

FIG. 1 is a configuration diagram of an X-ray inspection apparatus according to an embodiment; FIG. 2 is a schematic configuration diagram of an inside of a shield box illustrated in FIG. 1; and FIG. 3 is a block diagram illustrating an X-ray sensor unit, a control unit, and a sensitivity correction unit provided in the X-ray inspection apparatus. An X-ray inspection apparatus 1 illustrated in FIG. 1 generates an X-ray transmission image of an article G while conveying the article G, and inspects the article G based on the X-ray transmission image. The article G before the inspection is carried into the X-ray inspection apparatus 1 by a carry-in conveyor 51. The inspected article G is carried out from the X-ray inspection apparatus 1 by a carry-out conveyor 52. In one example, the X-ray inspection apparatus 1 can inspect the article G by a time delay integration method (TDI method). In addition, the X-ray inspection apparatus 1 can determine a state of the X-ray sensor unit 7 at the time of time delay integration driving (details will be described later).

The X-ray inspection apparatus 1 includes an apparatus main body 2, support legs 3, a shield box 4, a conveyance unit 5, an X-ray irradiation unit 6, an X-ray sensor unit 7, a display operation unit 8, and a control unit 9. The apparatus main body 2 accommodates the control unit 9 and the like. The support legs 3 support the apparatus main body 2. The shield box 4 is provided in the apparatus main body 2. The shield box 4 is a housing that prevents leakage of X-rays (electromagnetic waves) to an outside. An inspection chamber R in which inspection of the article G is performed by X-rays is provided inside the shield box 4. A carry-in port 4a and a carry-out port 4b are formed in the shield box 4. The article G before the inspection is carried into the inspection chamber R from the carry-in conveyor 51 via the carry-in port 4a. The inspected article G is carried out from the inspection chamber R to the carry-out conveyor 52 via the carry-out port 4b.

The conveyance unit 5 is an unit that conveys the article G, and is disposed so as to pass through the center of the shield box 4. The conveyance unit 5 conveys the article G along a conveyance direction A from the carry-in port 4a to the carry-out port 4b via the inspection chamber R. The conveyance unit 5 is, for example, a belt conveyor extended between the carry-in port 4a and the carry-out port 4b. The conveyance unit 5 may protrude outward from the carry-in port 4a and the carry-out port 4b.

As illustrated in FIGS. 1 and 2, the X-ray irradiation unit 6 is an electromagnetic wave irradiation unit (X-ray source) disposed in the shield box 4. The X-rays emitted from the X-ray irradiation unit 6 include X-rays in various energy regions from low energy (long wavelength) to high energy (short wavelength). Therefore, the X-ray irradiation unit 6 irradiates the article G conveyed by the conveyance unit 5 with X-rays in a plurality of energy regions. Immediately after the activation of the X-ray irradiation unit 6, the output of the X-rays may be unstable. Therefore, the X-ray irradiation (that is, idling of the X-ray irradiation unit 6) by the X-ray irradiation unit 6 may be performed after the activation of the X-ray inspection apparatus 1 and before the inspection of the article G. Note that "low" and "high" in the low energy and the high energy described above indicate relatively "low" and "high" in the plurality of energy regions irradiated from the X-ray irradiation unit 6, and do not indicate a specific range.

The X-ray sensor unit 7 is an apparatus that detects an electromagnetic wave. The X-ray sensor unit 7 is disposed at a position facing the X-ray irradiation unit 6 in a vertical direction in the shield box 4. As illustrated in FIG. 3, the X-ray sensor unit 7 has an X-ray detection unit 15 that detects X-rays by photon counting, and an image generation unit 16 that generates an image based on a detection result output from the X-ray detection unit 15.

The X-ray detection unit 15 is a sensor unit including eight sensor groups BS1 to BS8 and a calculation unit 15a. For example, the sensor groups BS1 to BS8 are arranged in order along a direction (arrangement direction) orthogonal to the conveyance direction A in a plan view. Each of the sensor groups BS1 to BS8 has a plurality of sensors 11 disposed two-dimensionally. The sensor groups BS1 to BS8 have the same number of sensors 11, but are not limited thereto. In each of the sensor groups BS1 to BS8, the number of sensors 11 arranged along the conveyance direction A is, for example, eight or more and 128 or less, and the number of sensors 11 arranged along the arrangement direction is, for example, 100 or more and 550 or less. Hereinafter, an aggregate of the plurality of sensors 11 arranged along the conveyance direction A may be referred to as a line sensor. The number of sensor groups included in the X-ray detection unit 15 is not limited to eight.

Each of the plurality of sensors 11 is a direct conversion type detection unit capable of detecting X-rays by photon counting, and is, for example, a multi-energy sensor that detects X-rays of each of a plurality of energy regions transmitting the article G. The sensor 11 includes, for example, a photon detection type sensor such as a CdTe semiconductor detector. In the sensor 11, for example, electron-hole pairs are generated by arrival of photons of X-rays. Energy (photon energy) is obtained by the generation of the electron-hole pairs.

The calculation unit 15a receives energy obtained by the sensor groups BS1 to BS8 and performs photon counting processing (photon counting) based on the energy. The calculation unit 15a includes, for example, a central processing unit (CPU), a read only memory (ROM), a random access memory (RAM), and the like. The calculation unit 15a may have a calculation processing unit such as CPUs corresponding to each of the sensor groups BS1 to BS8. Although not illustrated, the calculation unit 15a may be provided with a transfer unit or the like that receives energy output from the sensor groups BS1 to BS8 and outputs signals corresponding to the energy to the calculation processing unit. Since the calculation load of the counting processing by the calculation unit 15a is high, the calculation unit 15a tends to generate heat at the time of operating the X-ray inspection apparatus 1.

The calculation unit 15a discriminates photon energy of the X-rays detected based on an arbitrary threshold into two or more energy regions. As a result, the calculation unit 15a can perform the photon counting of each energy region. In one example, the calculation unit 15a classifies the detected photon energy of the X-rays into at least a first energy region and a second energy region higher than the first energy region by using the arbitrary threshold. The calculation unit 15a outputs the classified signal (detection result signal) corresponding to the X-ray detection result to the image generation unit 16. The arbitrary threshold is, for example, one or more values (unit: keV) set by the control unit 9. For example, Japanese Patent Application No. 2022-37999 (Japanese Unexamined Patent Publication No. 2023-132587) incorporated herein by reference, describes a method for setting an arbitrary threshold.

At least when the X-ray inspection apparatus 1 is activated, sensitivity correction (calibration) of the X-ray detection unit 15 is performed. For example, the arbitrary threshold is set during the sensitivity correction of the X-ray inspection apparatus 1. The sensitivity correction of the X-ray detection unit 15 corresponds to correction of an output difference between the sensors 11 included in the X-ray detection unit 15.

During the operation of the X-ray inspection apparatus 1, the temperature of the X-ray sensor unit 7 increases due to heat generation of at least one of the sensor 11 and the calculation unit 15a. The temperature rise of the X-ray sensor unit 7 may destabilize the output of the X-ray sensor unit 7 particularly immediately after the activation of the X-ray inspection apparatus 1. As a specific example, due to the temperature rise of the X-ray sensor unit 7, a counting processing accuracy of at least one sensor 11 is deteriorated, and a wrong counting number may be output. As a result, an inappropriate X-ray image can be generated. Therefore, the X-ray sensor unit 7 has a cooling element (not illustrated) that cools the X-ray sensor unit 7 in addition to the sensor 11. The temperature change of the X-ray sensor unit 7 can be suppressed by operating the cooling element during the operation of the X-ray inspection apparatus 1. For example, after the elapse of a predetermined period from the start of the X-ray detection by the X-ray sensor unit 7, the X-ray sensor unit 7 detects X-rays serving as a reference of the sensitivity correction and not transmitted the article G. The predetermined period is, for example, ten seconds or more, eight seconds or more, six seconds or more, or five seconds or more, but is not limited thereto. The predetermined period may be adjusted depending on the type, specification, and installation environment of the X-ray inspection apparatus 1.

From the viewpoint of power consumption and the like, the predetermined period may be set as short as possible. The cooling element is, for example, a Peltier element.

In general, a period required from the start of the X-ray detection by the X-ray sensor unit 7 to the stabilization of the output of the X-ray sensor unit 7 is equal to or longer than a period required from the start of the X-ray irradiation by the X-ray irradiation unit 6 to the stabilization of the output of the X-ray irradiation (period in which the irradiation of the X-ray source is stabilized). Therefore, the predetermined period is equal to or longer than the period required from the start of the X-ray detection by the X-ray sensor unit 7 until the stabilization of the output of the X-ray sensor unit 7. Similarly, the predetermined period is equal to or longer than the period in which the irradiation of the X-ray source is stabilized. Therefore, from the viewpoint of shortening the sensitivity correction of the X-ray sensor unit 7, at least the X-ray detection by the X-ray sensor unit 7 may be started when the X-ray inspection apparatus 1 is activated. From the viewpoint of stabilizing the output of the X-ray sensor unit 7, the X-ray irradiation unit 6 starts the X-ray irradiation during the predetermined period. In this case, the X-ray irradiation is started so that the X-ray irradiation is stabilized by the end of the predetermined period. In the sensitivity correction, the X-ray irradiation by the X-ray irradiation unit 6 may be started simultaneously with the start of the X-ray detection by the X-ray sensor unit 7.

The image generation unit 16 develops a signal (for example, the detection result signal) output from the X-ray detection unit 15 into a two-dimensional image on a memory. The image generation unit 16 is mainly configured by, for example, a graphics processing unit (GPU). The memory in which the two-dimensional image is developed is, for example, a memory included in the GPU, but is not limited thereto. The image generation unit 16 generates, for example, two or more X-ray transmission images corresponding to two or more energy regions based on the X-ray detection result by the X-ray detection unit 15. Each X-ray transmission image may be an image (hereinafter, simply referred to as an "inspection image") used for inspection of the article G, an image (hereinafter, simply referred to as a "threshold setting image") for setting the arbitrary threshold, or an image (hereinafter, simply referred to as a "determination image") for determining the state of the X-ray sensor unit 7. The inspection image is generated during the inspection of the article G by the X-ray inspection apparatus 1. The threshold setting image is generated, for example, during sensitivity correction or the like of the X-ray inspection apparatus 1. The determination image is generated, for example, during the determination of the state of the X-ray sensor unit 7 by the X-ray inspection apparatus 1. The determination of the state of the X-ray sensor unit 7 may be performed, for example, during the sensitivity correction or the like. Therefore, the determination image may be generated during the sensitivity correction of the X-ray inspection apparatus 1. For example, the image generation unit 16 may generate an entire transmission image corresponding to all the X-rays in the plurality of energy regions based on the detection result as the X-ray transmission image.

As illustrated in FIG. 1, the display operation unit 8 is an unit (display unit) provided in the apparatus main body 2. The display operation unit 8 displays various types of information and receives an input operation of various conditions from the outside. The display operation unit 8 is, for example, a liquid crystal display, and displays an operation screen as a touch panel. In this case, an operator can input various conditions via the display operation unit 8. As another example, the operator can switch between a mode (first mode) in which the article G is inspected and a mode (second mode) in which the state of the X-ray sensor unit 7 at the time of time delay integration driving is determined via the display operation unit 8.

The control unit 9 is disposed inside the apparatus main body 2. The control unit 9 controls the operation of each unit of the X-ray inspection apparatus 1. The control unit 9 includes a central processing unit (CPU), a read only memory (ROM), a random access memory (RAM), and the like. A program for controlling the X-ray inspection apparatus 1 is recorded in the ROM. The control unit 9 also functions as an inspection unit for inspecting the article G based on the image generated from the output result of the X-ray sensor unit 7. The control unit 9 also functions as a state determination unit for determining the state of the X-ray sensor unit 7 at the time of time delay integration driving. Therefore, the control unit 9 has a first mode for inspecting the article G and a second mode for determining the state of the X-ray sensor unit 7 at the time of time delay integration driving.

In the first mode, the control unit 9 performs inspection of the article G based on X-rays detected by the X-ray sensor unit 7 and transmitted the article G. At this time, the inspection of the article G is performed using the inspection image generated based on the X-rays. Subsequently, the control unit 9 determines whether or not the article G is a non-defective product. Subsequently, the control unit 9 outputs a determination result as to whether or not the article G is a non-defective product, and stores the determination result. At this time, an image or the like used to generate the determination result may be stored in association with each other. Note that the control unit 9 inspects, for example, the presence or absence of a foreign substance, the presence or absence of a crack, and the like with respect to the article G, but is not limited thereto. In a case where the article G is wrapped with a sheet-like packaging material, and the like, the control unit 9 can also inspect breakage of the packaging material, seal failure (seal biting) of the packaging material, and the like.

In the second mode, the control unit 9 determines, for example, at least one of the transmission state from the X-ray detection unit 15 to the image generation unit 16 at the time of time delay integration driving and the state of the image generation operation by the image generation unit 16 at the time of time delay integration driving. In the former, for example, the presence or absence of an abnormality related to signal transmission from the sensor 11 to the calculation unit 15a, the presence or absence of an abnormality related to signal transmission of a transfer unit or the like in the calculation unit 15a, the presence or absence of an abnormality related to processing in the calculation unit 15a, and the like are determined.

In the second mode, the X-ray detection unit 15 of the X-ray sensor unit 7 detects X-rays not transmitted the article G. Subsequently, the image generation unit 16 generates a determination image (first image) based on a detection result output from the X-ray detection unit 15 at a predetermined timing (time t1). As a result, the image can be generated at the time of normal driving of the X-ray inspection apparatus 1. Subsequently, the image generation unit 16 integrates detection results output from the X-ray detection unit 15 until a timing (time t2) after the predetermined timing, and generates another determination image (second image). In other words, the image generation unit 16 integrates the detection results output from the X-ray detection unit 15 from the time t1 to the time t2 to generate the second image.

As a result, the image at the time of time delay integration driving of the X-ray inspection apparatus 1 can be generated.

Subsequently, the control unit 9 compares the first image with the second image to determine the state of the X-ray sensor unit 7 at the time of time delay integration driving. In one example, the control unit 9 compares a luminance of the first image with a luminance of the second image. Then, the control unit 9 determines whether or not the second image is darker than the first image by a predetermined ratio or more. In the determination, for example, a difference (average luminance difference) between an average luminance of the first image and an average luminance of the second image and a difference (maximum luminance difference) between a maximum luminance of the first image and a maximum luminance of the second image are used. For example, when the average luminance difference is larger than 0.5% and the maximum luminance difference is larger than 2.0%, it is determined that the second image is darker than the first image by a predetermined ratio or more. In this case, it is determined that a drift of the luminance at the time of the time delay integration driving is excessive, and the control unit 9 determines that the X-ray sensor unit 7 is defective. The cause of the determination that the X-ray sensor unit 7 is defective (for example, a transmission state from the X-ray detection unit 15 to the image generation unit 16 at the time of time delay integration driving, an image generation operation by the image generation unit 16 at the time of time delay integration driving, and the like) can be estimated by, for example, a relationship or the like between the average luminance difference and the maximum luminance difference. The control unit 9 compares a luminance of each pixel in the first image with a luminance of each pixel in the second image. At this time, the average luminance difference and the maximum luminance difference in each of the sensor groups BS1 to BS8 may be used. In this case, it is possible to determine the presence or absence of an abnormality of each of the sensor groups BS1 to BS8. Hereinafter, a ratio obtained by dividing the luminance at the time of generating the second image by the luminance at the time of generating the first image in each sensor 11 corresponds to a drift rate of the sensor 11. The larger the drift rate of the sensor 11 is, the more a defect may occur in the X-ray transmission image generated at the time of time delay integration driving. The drift rate of the sensor 11 may be a value (%) obtained by "Equation: 100−luminance of sensor 11 in second image/luminance of sensor 11 in first image× 100" or a value (%) obtained by "Equation: luminance of sensor 11 in second image/luminance of sensor 11 in first image×100".

The sensitivity correction unit 20 performs sensitivity correction of the X-ray detection unit 15 based on untransmitted X-rays. The sensitivity correction unit 20 includes a CPU, a ROM, a RAM, and the like. The sensitivity correction unit 20 may be a part of the control unit 9. The sensitivity correction unit 20 performs the sensitivity correction at least when the X-ray inspection apparatus 1 is activated. In the sensitivity correction of the X-ray detection unit 15 by the sensitivity correction unit 20, for example, a bright level is acquired based on the untransmitted X-rays. The bright level is the number of photon counts detected when the X-rays not transmitted the article G are incident on the X-ray detection unit 15. The bright level may change depending on the output or the like of the X-ray irradiation unit 6. Therefore, the number of bright levels is not limited to one, and may be plural. For example, the bright level has at least a maximum bright level obtained when the output of the X-ray irradiation unit 6 is 100% and an intermediate bright level (gray level) obtained when the output of the X-ray irradiation unit 6 is 50%. In one example, the acquisition of a dark level by the X-ray detection unit 15 may not be performed in the sensitivity correction. In this case, simply the fact that the number of detected photons is 0 may be set in advance as the dark level. Alternatively, in the sensitivity correction, when the number of photons detected by the X-ray detection unit 15 is 0, the dark level may be set. When the sensitivity correction is performed by the sensitivity correction unit 20, the control unit 9 determines the state of the X-ray sensor unit 7 at the time of time delay integration driving. For example, every time the sensitivity correction is performed by the sensitivity correction unit 20, the control unit 9 determines the state of the X-ray sensor unit 7 at the time of time delay integration driving.

Figure 4:
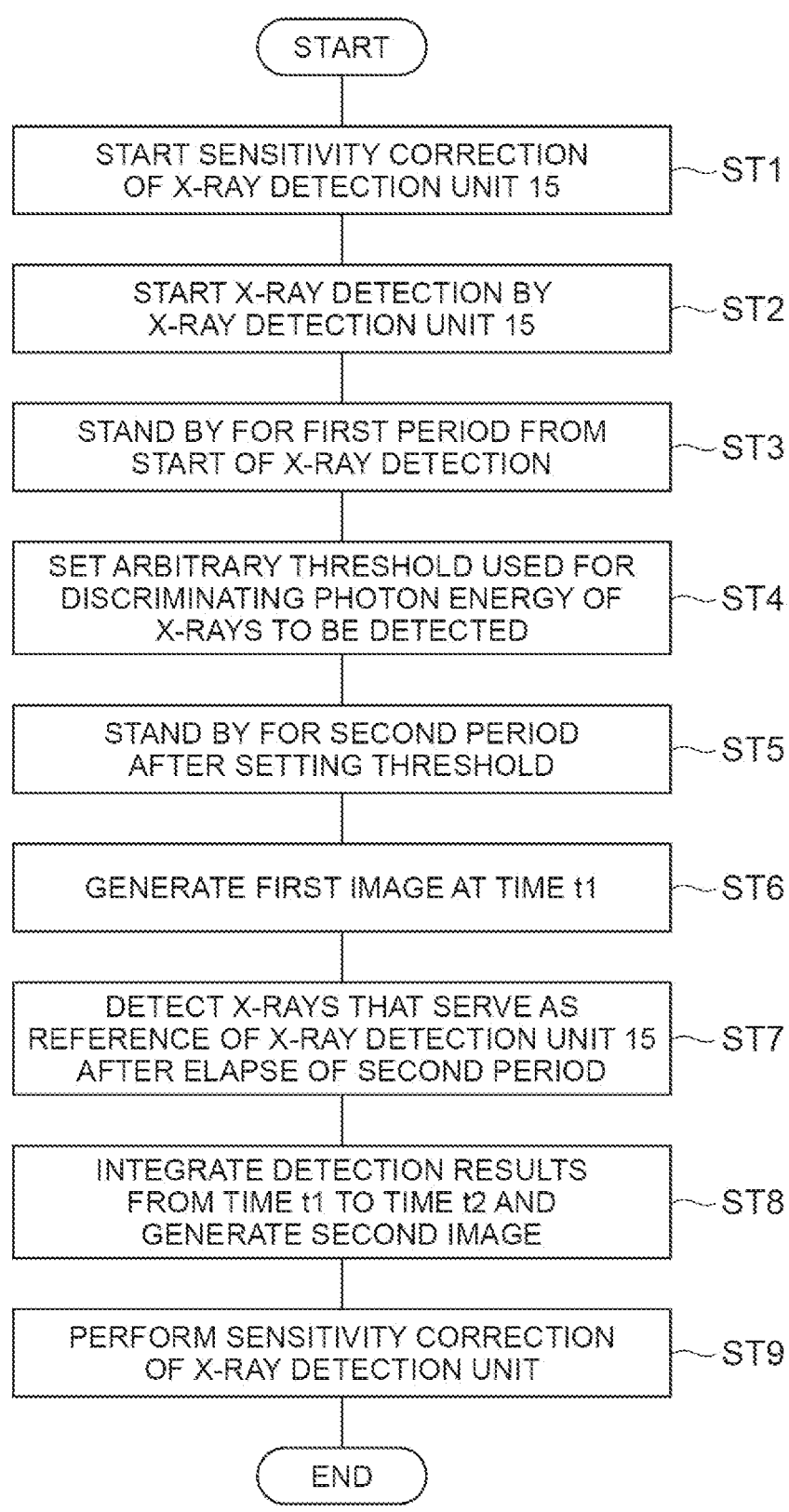
FIG. 4 is a flowchart for describing a sensitivity correction method and an inspection method of the X-ray sensor unit.

Next, an example of an inspection method of the X-ray sensor unit 7 included in the X-ray inspection apparatus 1 according to the present embodiment will be described with reference to FIG. 4. In one example, the inspection method is performed during the sensitivity correction of the X-ray detection unit 15 included in the X-ray sensor unit 7. Therefore, a sensitivity correction method of the X-ray detection unit 15 and an inspection method of the X-ray sensor unit will be described below. FIG. 4 is a flowchart for describing the sensitivity correction method and the inspection method of the X-ray sensor unit.

As illustrated in FIG. 4, first, the sensitivity correction of the X-ray detection unit 15 included in the X-ray sensor unit 7 is started when the X-ray inspection apparatus 1 is activated (step ST1). In step ST1, the X-ray inspection apparatus 1 is activated, and an inspection parameter, an initial value of a threshold, and the like are set in the X-ray sensor unit 7. Subsequently, X-ray detection by the X-ray detection unit 15 is started (step ST2). In one example, in step ST2, X-ray irradiation by the X-ray irradiation unit 6 is started simultaneously with the X-ray detection by the X-ray detection unit 15, but is not limited thereto. In step ST2, the X-ray detection result by the X-ray detection unit 15 is not used in the sensitivity correction. As a result, unstable detection results are less likely to be used.

Next, the processing stands by for a first period from the start of the X-ray detection by the X-ray detection unit 15 (step ST3). In step ST3, during the first period, the X-ray detection by the X-ray detection unit 15 is maintained, and the X-ray detection unit 15 generates heat. In step ST3, the cooling element of the X-ray detection unit 15 also operates, and the temperature of the X-ray detection unit 15 is adjusted. Similarly, during the first period, the X-ray irradiation by the X-ray irradiation unit 6 is maintained. As a result, an output of the X-ray irradiation unit 6 is stabilized. When the X-ray irradiation by the X-ray irradiation unit 6 is not started in step ST2, the X-ray irradiation by the X-ray irradiation unit 6 is started in step ST3. In other words, in a case where the X-ray irradiation by the X-ray irradiation unit 6 is not started in step ST2, the X-ray irradiation by the X-ray irradiation unit 6 is started during the first period. Also in step ST3, the X-ray detection result by the X-ray detection unit 15 is not used in the sensitivity correction. As a result, unstable detection results are less likely to be used.

Subsequently, after the elapse of the first period from the start of X-ray detection by the X-ray detection unit 15 (that is, after step ST3), an arbitrary threshold used for discriminating photon energy of the X-rays to be detected is set (step ST4). In step ST4, first, untransmitted X-rays are detected by the X-ray detection unit 15 using the photon counting. Then, the arbitrary threshold is set using the detection result of the X-ray detection unit 15 in step ST4. For example, Japanese Patent Application No. 2022-37999 (Japanese Unexamined Patent Publication No. 2023-132587) incorporated herein by reference, describes an example of a method of setting the arbitrary threshold.

The processing stands by for a second period after setting the threshold (step ST5). By performing step ST5, the sensitivity correction of the X-ray detection unit 15 can be more appropriately performed. In step ST5, the X-ray detection by the X-ray detection unit 15 is maintained during the second period. On the other hand, in step ST5, the X-ray detection result by the X-ray detection unit 15 is not used in the sensitivity correction. The second period is, for example, ten seconds or more, eight seconds or more, or six seconds or more, but is not limited thereto. The second period may be adjusted depending on the type, specification, and installation environment of the X-ray inspection apparatus 1. From the viewpoint of power consumption and the like, the second period may be set as short as possible.

The first image is generated based on the detection result output from the X-ray detection unit 15 at the timing (time t1) in the second period after the elapse of a predetermined period from the setting of the threshold (step ST6). In step ST6, for example, the first image is generated at a timing at which five seconds or more have elapsed from the start of step ST5. By performing step ST6 at the time t1 after the elapse of the predetermined period from the start of step ST5 in this manner, the state of the X-ray sensor unit 7 can be accurately determined. After step ST6, the X-ray inspection apparatus 1 performs time delay integration driving. As a result, the X-ray inspection apparatus 1 integrates detection results output from the X-ray detection unit 15.

Next, after step ST5, X-rays serving as a reference of the X-ray detection unit 15 not transmitted the article G are detected (step ST7). In step ST7, for example, for each sensor 11, acquisition of a bright level, acquisition of a 0 point, calculation of a span coefficient value, and the like are performed. As a result, a calibration curve may be created. In step ST7, acquisition of a dark level may be performed.

Next, the detection results output from the X-ray detection unit 15 from the time t1 to the time t2 are integrated to generate the second image (step ST8). After step ST8, the first image and the second image are compared to determine the state of the X-ray sensor unit 7 at the time of time delay integration driving. As described above, the state of the X-ray sensor unit 7 is determined by determining whether or not the second image is darker than the first image by a predetermined ratio or more.

Then, the sensitivity correction of the X-ray detection unit 15 is completed (step ST9). In step ST9, the acquired bright level, the calculated value, and the like are set in each sensor 11 of the X-ray detection unit 15. As described above, the sensitivity correction of the X-ray detection unit 15 performed when the X-ray inspection apparatus 1 is activated is completed. For example, after the sensitivity correction method is performed when the X-ray inspection apparatus 1 is activated, every time the sensitivity correction method is performed, at least one of steps ST1 to ST9 described above is performed.

Figure 5:
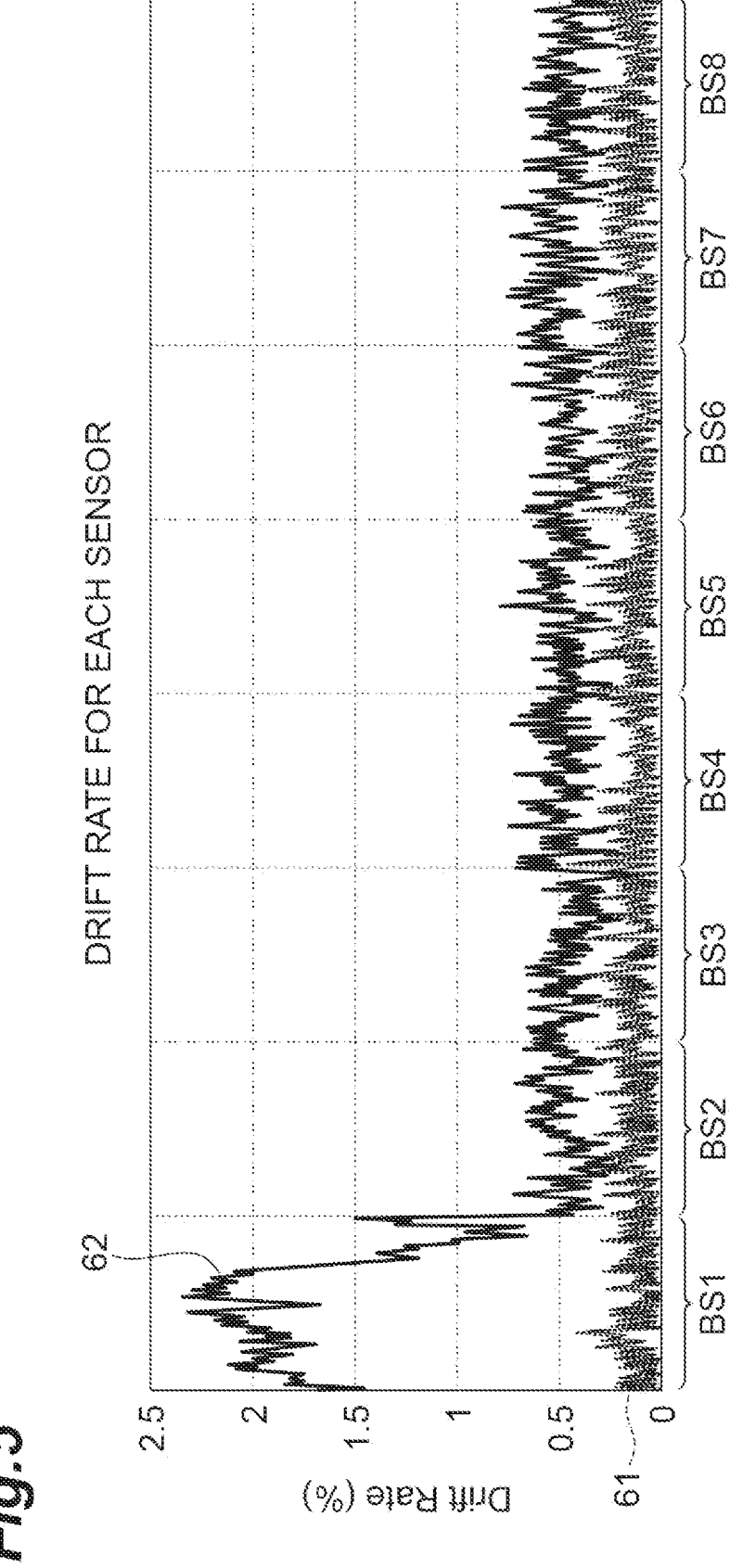
FIG. 5 is a graph illustrating a drift rate for each sensor.
Figure 6:
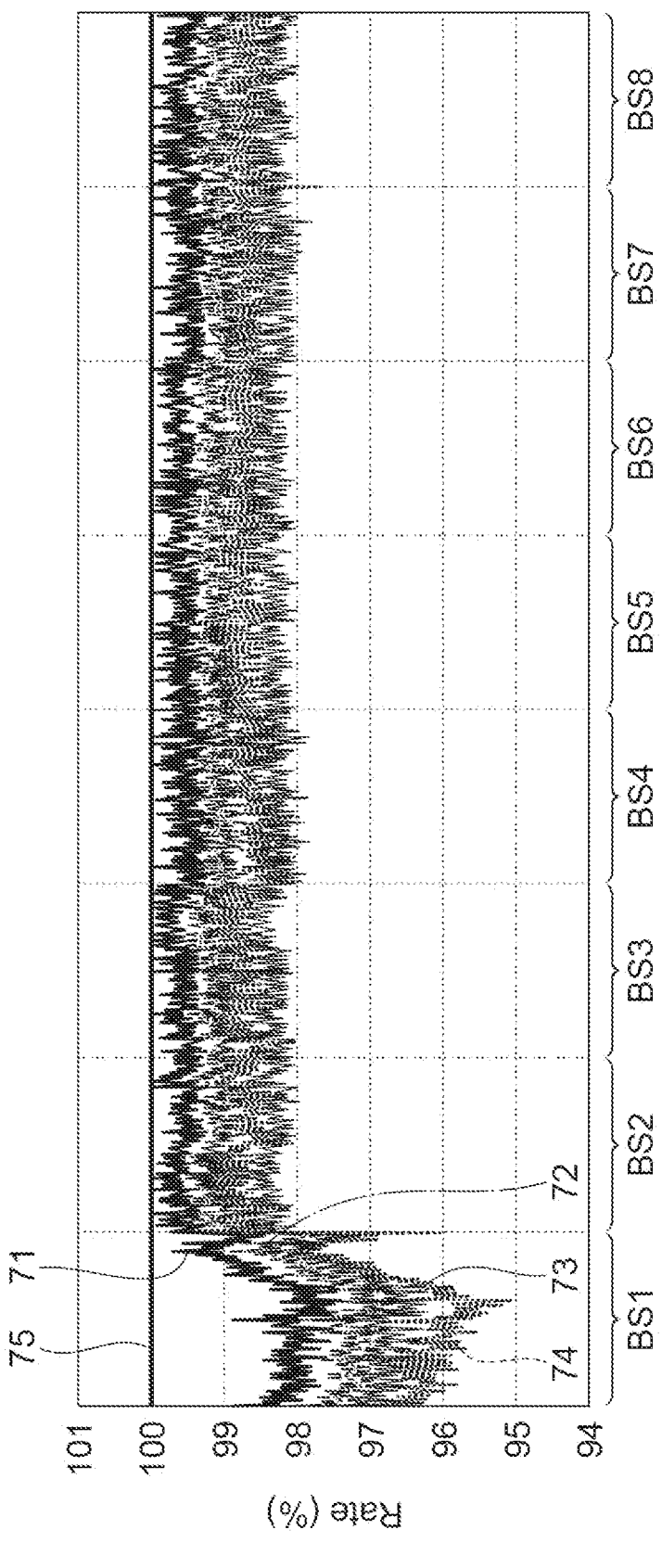
FIG. 6 is a graph illustrating a change in the drift rate of the X-ray sensor unit depending on a period in which a time delay integration is performed.

The operational effects obtained by the X-ray inspection apparatus 1 according to the present embodiment described above will be described with reference to FIGS. 5 and 6. FIG. 5 is a graph illustrating a drift rate for each sensor. FIG. 6 is a graph illustrating a change in the drift rate of the X-ray sensor unit depending on a period in which a time delay integration is performed. In each of FIGS. 5 and 6, a vertical axis indicates a drift rate, and a horizontal axis indicates the number of sensors 11 along the arrangement direction. Data at a left end on the horizontal axis indicates a drift rate of the line sensor located at one end in the arrangement direction and extending along the conveyance direction A, and data at a right end on the horizontal axis indicates a drift rate of the line sensor located at the other end in the arrangement direction. "BS1" described on the horizontal axis in FIGS. 5 and 6 indicates a sensor group BS1. Therefore, the drift rate of each line sensor included in the sensor group BS1 is indicated within the range of "BS1" described on the horizontal axis in FIGS. 5 and 6. The measurement results illustrated in FIGS. 5 and 6 were obtained under the conditions of a tube voltage: 75 kV, a tube current: 1.0 mA, a conveying speed: 15 m/min, and an integration time: 10 seconds.

In FIG. 5, a plot 61 indicates a measurement result of the drift rate of the X-ray sensor unit which is determined to be a non-defective product later, and a plot 62 indicates a measurement result of the drift rate of the X-ray sensor unit (hereinafter, simply referred to as a "defective X-ray sensor unit") which is determined to be a defective product later. In the plot 61, luminance differences of almost all the sensors are 0.5% or less. In the plot 61, the average luminance difference of each line sensor is 0.15% and the maximum luminance difference of the line sensor is 0.48%. On the other hand, in the plot 62, the luminance differences of almost all the line sensors included in the sensor group BS1 are obviously larger than 0.5%. The maximum luminance difference of the line sensors included in the sensor group BS1 exceeds 2.0%. In addition, the luminance difference between the line sensors included in the sensor groups BS2 to BS8 is around 0.5%. In the plot 62, the average luminance difference of each line sensor is 0.64% and the maximum luminance difference of the line sensor is 2.34%.

In FIG. 6, a plot 71 indicates a measurement result of the drift rate of the defective X-ray sensor unit when the integration time is 10 seconds, a plot 72 indicates a measurement result of the drift rate of the defective X-ray sensor unit when the integration time is 30 seconds, a plot 73 indicates a measurement result of the drift rate of the defective X-ray sensor unit when the integration time is 60 seconds, and a plot 74 indicates a measurement result of the drift rate of the defective X-ray sensor unit when the integration time is 170 seconds. In addition, a plot 75 indicates a measurement result of the drift rate of the defective x-ray sensor unit when the integration time is 0 seconds. In other words, the plot 75 indicates the luminance difference between the first image generated at the time t1 and the second image generated at the time t2. Thus, each of the plots 71 to 74 is data obtained at the time of time delay integration driving of the X-ray inspection apparatus including the defective X-ray sensor unit. On the other hand, the plot 75 is data obtained at the time of normal driving of the X-ray inspection apparatus including the defective X-ray sensor unit.

As illustrated in FIG. 6, in the X-ray sensor unit which is a defective product, no defect occurs in the normal operation, and on the other hand, the longer the integration time, the higher the drift rate. From this data, it can be seen that when the X-ray sensor unit which is a defective product is time-delayed integral driven, there is a high possibility that a defect occurs in the generation of the X-ray transmission image with the driving time.

On the other hand, in the X-ray inspection apparatus 1 according to the present embodiment, the first image generated based on the detection result output from the X-ray detection unit 15 at the time t1 is compared with the second image generated by integrating the detection results output from the X-ray detection unit 15 until the time t2 after the time t1 in the second mode. As a result, the output of the X-ray detection unit 15 at the time of normal driving can be compared with the output of the X-ray detection unit 15 at the time of time delay integration driving. By using this comparison, for example, it is possible to easily determine whether or not there is a defect in the X-ray sensor unit 7 at the time of time delay integration driving. Therefore, by using the X-ray inspection apparatus 1, the state of the X-ray sensor unit 7 at the time of time delay integration driving can be satisfactorily determined.

In one example, the X-ray inspection apparatus 1 may include the sensitivity correction unit 20 that performs the sensitivity correction of the X-ray detection unit 15 based on the untransmitted X-rays, and the control unit 9 may determine the state of the X-ray sensor unit 7 at the time of time delay integration driving when the sensitivity correction is performed by the sensitivity correction unit 20. In this case, for example, before the inspection or the like of the article G by the X-ray inspection apparatus 1, the state of the X-ray sensor unit 7 at the time of the time delay integration driving can be satisfactorily determined.

In one example, the control unit 9 determines that the X-ray sensor unit 7 is defective when the second image is darker than the first image by a predetermined ratio or more, but is not limited thereto. The control unit 9 may determine that the X-ray sensor unit 7 is defective when the second image is brighter than the first image by a predetermined ratio or more.

In one example, in the second mode, the control unit 9 may determine at least one of the transmission state from the X-ray detection unit 15 to the image generation unit 16 at the time of time delay integration driving and the state of the image generation operation by the image generation unit 16 at the time of time delay integration driving.

Although the embodiment of the present disclosure has been described above, the present disclosure is not necessarily limited to the above-described embodiment, and various modifications can be made without departing from the gist thereof. For example, in the above embodiment, the state of the X-ray sensor unit is determined during the sensitivity correction of the X-ray detection unit, but is not limited thereto. For example, the state of the X-ray sensor unit may be determined after the sensitivity correction of the X-ray detection unit. In this case, steps ST1 to ST9 are appropriately rearranged.

In the above embodiment, the image generation unit is included in the X-ray sensor unit and independent of the control unit, but is not limited thereto. The image generation unit may be a part of the control unit. In this case, a part of the control unit is considered to be included in the X-ray sensor unit.

REFERENCE SIGNS LIST

1 X-ray inspection apparatus
3 support leg
4 shield box
4a carry-in port
4b carry-out port
5 conveyance unit
6 X-ray irradiation unit
7 X-ray sensor unit
8 display operation unit
9 control unit
11 sensor
15 X-ray detection unit

15a calculation unit
16 image generation unit
20 sensitivity correction unit
A conveyance direction
G article

What is claimed is:

1. An X-ray inspection apparatus comprising:
a conveyance unit configured to convey an article;
an irradiation unit configured to irradiate the article conveyed by the conveyance unit with X-rays;
an X-ray sensor unit including a sensor unit configured to detect the X-rays by photon counting and an image generation unit configured to generate an image based on a detection result output from the sensor unit;
a control unit having a first mode for inspecting the article based on the image and a second mode for determining a state of the X-ray sensor unit at a time of time delay integration driving; and
a sensitivity correction unit configured to perform sensitivity correction of the sensor unit based on the X-rays not transmitted to the article, wherein
in the second mode,
the sensor unit is configured to detect X-rays not transmitted to the article, and
the control unit is configured to compare a first image generated based on a detection result output from the sensor unit at a time t1 with a second image generated by integrating detection results output from the sensor unit until a time t2 after the time t1 to determine the state of the X-ray sensor unit at the time of time delay integration driving, when the sensitivity correction is performed by the sensitivity correction unit.

2. The X-ray inspection apparatus according to claim 1, wherein
the control unit is configured to determine that the X-ray sensor unit is defective when the second image is darker than the first image by a predetermined ratio or more.

3. The X-ray inspection apparatus according to claim 1, wherein
in the second mode, the control unit is configured to determine a transmission state from the sensor unit to the image generation unit at the time of time delay integration driving or a state of an image generation operation by the image generation unit at the time of time delay integration driving.

4. An inspection method of an X-ray sensor unit including a sensor unit configured to detect X-rays by photon counting and an image generation unit configured to generate an image based on a detection result output from the sensor unit, the inspection method comprising:
performing sensitivity correction of the sensor unit based on the X-rays not transmitted to an article; and
comparing a first image generated based on a detection result output from the sensor unit at a time t1 with a second image generated by integrating detection results output from the sensor unit until a time t2 after the time t1, and determining a state of the X-ray sensor unit at a time of time delay integration driving, during the sensitivity correction.

* * * * *